United States Patent [19]

Ohkawa et al.

[11] Patent Number: 5,686,291
[45] Date of Patent: Nov. 11, 1997

[54] CORYNEBACTERIUM SP. N HAVING DECOMPOSABILITY FOR ETHANOLAMINES

[75] Inventors: Tadashi Ohkawa; Hiromi Aoki; Keizo Aiba, all of Koka-gun; Takashi Yoneshima, Yasu-gun; Koji Nakatani, Toyama; Goichi Sugasawa, Takaoka, all of Japan

[73] Assignees: Kabushiki Kaisha Neos, Hyogo-ken; Nachi-Fujikoshi Corp., Tokyama-ken, both of Japan

[21] Appl. No.: 722,925

[22] Filed: Sep. 30, 1996

[30] Foreign Application Priority Data

Oct. 4, 1995 [JP] Japan .................................. 7-257448
Oct. 9, 1995 [JP] Japan .................................. 7-286361

[51] Int. Cl.⁶ .................................................. C12N 1/26
[52] U.S. Cl. .................................. 435/252.1; 435/262.5
[58] Field of Search ............................. 435/170, 252.1, 435/262.5

[56] References Cited

FOREIGN PATENT DOCUMENTS 109975  4/1990  Japan .
335688  12/1994  Japan .

OTHER PUBLICATIONS

Shukla and Turner. Microbial metabolism of amino alcohols. Biochem J. 186:13–19. Oct. 1980.

Calabrese et al. Mobility and enganced biodegradation of a dilute waste oil emulsion during land treatment. J. Ind. Microbiol. 12:13–20 Aug. 20, 1993.

*Primary Examiner*—David Guzo
*Assistant Examiner*—William Sandals
*Attorney, Agent, or Firm*—Watson Cole Stevens Davis, PLLC

[57] ABSTRACT

By utilizing Corynebacterium sp. N according to the present invention, massive amounts of the waste fluid containing high concentration ethanolamines can effectively be treated without causing an environmental pollution. According to the present invention, it is possible to treat the waste fluid containing ethanolamines in a small-scale manner. The apparatus for treating the waste fluid according to the present invention can readily be installed, and the initial and running costs such as a maintenance of the apparatus are inexpensive.

10 Claims, 6 Drawing Sheets

CORYNEBACTERIUM SP. N HAVING DECOMPOSABILITY FOR ETHANOLAMINES

FIELD OF INVENTION

The present invention relates to Corynebacterium Sp. N microorganisms exhibiting efficient ethanolamines decomposition effect, a process for treating an aqueous waste fluid containing ethanolamines by means of said microorganisms as well as a process for treating ammoniacal nitrogen in a waste fluid treated by said microorganisms and an apparatus therefor.

BACKGROUND OF THE INVENTION

Ethanolamines are employed as a rust preventive for a water-soluble machining oil, a detergent and the like. Although content of ethanolamines in the water-soluble machining oil and the like depends on the kind of metallic materials to be machined and the like, it generally ranges from 10 percent by weight to 40 percent by weight. In a factory where metallic materials are machined, massive amounts of waste fluid containing ethanolamines must be treated because the machining oil is used by diluting with water about 10–50 times. Although an aggregation method, an active sludge method, an active carbon adsorption method and the like are known as processes for treating an aqueous waste fluid containing ethanolamines, the ethanolamines, which are hard to decompose, cannot effectively be treated by these methods. From a viewpoint of the protection of the environment, it is disadvantageous to discharge insufficiently treated ethanolamines, which pose a problem to an ecosystem's safety.

Therefore, a combustion method is generally adopted which comprises impregnating a sawdust, and the like, with the waste fluid of the machining oil, and burning the impregnated sawdust and the like. However, this method poses a problem in that the combustion of ethanolamines produces harmful nitrogen oxides which become the cause of an air pollution.

Furthermore, in order to treat the waste fluid of the machining oil, a biological method has been proposed decomposing ethanolamines by the use of a specific microorganism, i.e. _Flavobacterium aquatile_ (cf. Japanese Patent Publication (KOKOKU) No. 109975/1990]. However, the decomposition effect of this biological method has been confirmed in the case where the concentration of ethanolamines is less than 0.1%. It would be difficult to effectively treat large quantities of the waste fluid of the machining oil containing about 1–4% of ethanolamines by means of said microorganism.

On the other hand, the aqueous waste fluid treated by the biological method contains harmful ammoniacal nitrogen which must be removed from the treated waste fluid. The aforesaid Japanese Patent Publication is silent about any treating method of the ammoniacal nitrogen.

An ammonia stripping method has widely been known as a treating method for ammoniacal nitrogen in an aqueous waste fluid [see, for example, Japanese Patent Publication (KOKAI) No. 335688/1994]. The ammonia stripping method utilizes the fact that the ammoniacal nitrogen is in an equilibrium condition between ammonium ion and free ammonia, said equilibrium condition depending on the pH and the temperature of the waste fluid. Most of the ammoniacal nitrogen in the waste fluid exists as ammonium ion at around a pH of 7, and about 90% of the ammoniacal nitrogen exists as free ammonia at around a pH of 11. Therefore, ammonia in the waste fluid can be diffused by contacting the ammonia with air or water vapor after adjusting pH of the waste fluid to around 11 by adding lime to the waste fluid.

However, the ammonia stripping method requires not only a large scale of equipment consisting of complex machinery and an ammonia stripping tower, which stores a large quantity of the waste fluid and effectively removes ammonia gas by blowing air into the waste fluid from the bottom to the top of the tower, but also an expensive initial and running cost such as maintenance, and the like.

Moreover, it is difficult for a private enterprise to establish such a large scale of equipment, such as the stripping tower and the facilities for the biological treatment of the waste fluid containing the amines in an environment such as factory wastes. In addition, it is difficult to control the biological treatment because the ammonia stripping process follows a process for confirming a completion of the biological treatment by indirect indices, such as pH, turbidity, and the like, of the waste fluid.

One object to the present invention is to provide novel microorganisms that effectively decompose a high concentration of ethanolamines as well as a process for treating an aqueous waste fluid containing ethanolamines by means of said microorganisms.

Another object of the present invention is to provide a process for treating an ammoniacal nitrogen in a waste fluid treated by said microorganisms and an apparatus therefor, said process and apparatus being small-scale, easily controllable, less expensive (low initial and running costs such as a maintenance), uncomplicated and easily manageable.

SUMMARY OF THE INVENTION

The present invention relates to the following Corynebacterium sp. N having a decomposition effect on ethanolamines: Corynebacterium sp. N1, corynebacterium sp. N2, (3) Corynebacterium sp. N3., Corynebacterium sp. N4 and (5) Corynebacterium sp. N5.

The present invention also relates to a process for treating an aqueous waste fluid containing ethanolamines by means of said microorganisms.

Furthermore, the present invention relates to a process for treating an ammoniacal nitrogen in a waste fluid treated by said microorganisms which comprises (i) removing the ingredients which inhibit the treatment by microorganisms, such as a preservative, a rust preventative and the like from the waste fluid, (ii) supplying the pretreated waste fluid to a semi-closed biological treatment tank equipped with an inlet and an outlet for a gas, (iii) adding the aforesaid microorganisms to said tank to decompose ethanolamines in the waste fluid into an ammonium ion, (iv) adding an alkali to said tank to produce free ammonia at a pH of more than 10, (v) discharging the free ammonia as an ammonia gas through the outlet of said tank, and (vi) subjecting the waste fluid in said tank to a post-treatment from the group consisting of agglomerative, precipitation and neutralization.

In addition, the present invention relates to an apparatus for treating an ammoniacal nitrogen in the waste fluid treated by the aforesaid microorganisms which comprises (i) a pretreatment tank for removing ingredients which inhibit the treatment by said microorganisms, such as a preservative, a rust preventative and the like from the waste fluid, and (ii) a semi-closed biological treatment tank equipped with an inlet for introducing the pretreated waste fluid, an inlet for introducing a blowing gas through said waste fluid, an outlet for discharging said blowing gas and any generated gas, which is connected with an absorption tower for ammonia gas, an inlet for introducing an alkali, a detector for detecting concentrations of ingredients in said waste fluid, and an outlet for discharging said waste fluid in order to subject said waste fluid to a post-treatment selected from the group consisting of agglomeration, precipitation and neutralization.

DETAILED EXPLANATION OF THE INVENTION

The aforementioned microorganisms according to the present invention were isolated from the active sludge in Kosei-cho (Shiga Prefecture, Japan). These microorganisms have the following mycological characteristics.

(1) corynebacterium sp. N1

A. Morphological characteristics
  i) Shape and size of a cell: spherical or rod-shaped cell having size of 0.4–0.6×0.6–2.0 µm.
  ii) Polymorphism of a cell: The cell has V-type and Y-type chains.
  iii) Mobility: Non
  iv) Sporulation: Non
  v) Gram stain: Change from positive to negative.

B. Cultural characteristic
  i) Nutrient agar (30° C., 5 days): Growth is excellent. The shape of the cultured strain is circular. Surface of the cultured strain is slightly rising and smooth. Although the color of the cultured strain is cream, it becomes yellow after longer cultivation.
  ii) Nutrient agar slant: Growth is excellent. Surface of the cultured strain is smooth. Although the color of the cultured strain is cream, it becomes yellow after longer cultivation.
  iii) Stab culture: The microorganism grows on the surface of standard agar medium, and liquefies gelatin.
  iv) Nutrient broth: The microorganism grows vigorously and forms a ring.

C. Physiological characteristics
  ii) Reduction of nitrate: The microorganism does not reduce nitrate.
  ii) Indole production: Negative
  iii) Hydrogen sulfide production: Negative
  iv) VP reaction: Negative
  v) Methyl red reaction: Negative
  vi) Hydrolysis of starch: Positive
  vii) Hydrolysis of gelatin: Positive
  viii) Decomposition of Tween 80: Positive
  ix) Hydrolysis of esculin: Positive
  x) Hydrolysis of casein: Positive
  xi) Egg yolk reaction: Transparentization
  xii) Reaction in the litmus milk: The microorganism reduces dye.
  xiii) Decomposition of arginine: Positive
  xiv) Urease: weakly positive
  xv) Catalase: Positive
  xvi) Oxidase: Negative
  xvii) OF test: Unchanged
  xviii) Pigments production: The microorganism does not produce water soluble pigments.
  xix) Temperature for growth: 4°–37° C.
  xx) Oxygen demand: Aerobic
  xxi) Formation of acids from the carbohydrates:

| glucose | + | maltose | + |
| sucrose | + | galactose | + |
| lactose | + | arabinose | + | xxii) Utilization as a carbon source and an energy source:

| glucose | + | maltose | + |
| sucrose | + | galactose | + |
| lactose | + | arabinose | + | xxiii) The pH value for growth: 5.0–8.5
  xxiv) Halotolerance: 2% NaCl
  xxv) Demand for growth factor: Non
  xxvi) G/C: 73.8%

(2) Corynebacterium sp. N2

A. Morphological characteristics
  i) Shape and size of a cell: Spherical or rod-shaped cell having size of 0.6–0.8×1.0–2.0 µm
  ii) Polymorphism of a cell: The cell has V-type and Y-type chains.
  iii) Mobility: Non
  iv) Sporulation: Non
  v) Gram stain: Change from positive to negative.

B. Cultural characteristics
  i) Nutrient agar (30° C., 5 days): Growth is excellent. The shape of the cultured strain is circular. Surface of the cultured strain is slightly rising and smooth. The color of the cultured strain is yellow.
  ii) Nutrient agar slant: Growth is excellent. Surface of the cultured strain is smooth. The color of the cultured strain is yellow.
  iii) Stab culture: The microorganism grows on the surface of standard agar medium, and liquefies gelatin.

iv) Nutrient broth: The microorganism forms a ring.

C. Physiological characteristics
  i) Reduction of nitrate: The microorganism does not reduce nitrate.
  ii) Indole production: Negative
  iii) Hydrogen sulfide production: Negative
  iv) VP reaction: Negative
  v) Methyl red reaction: Negative
  vi) Hydrolysis of starch: Negative
  vii) Hydrolysis of gelatin: Positive
  viii) Decomposition of Tween 80: Negative
  ix) Hydrolysis of esculin: Negative
  x) Hydrolysis of casein: Positive
  xi) Egg yolk reaction: Transparentization
  xii) Reaction in the litmus milk: The microorganism reduces dye, and liquefies the litmus milk after coagulation thereof.
  xiii) Decomposition of arginine: Positive
  xiv) Urease: Negative
  xv) Catalase: Positive
  xvi) Oxidase: Negative
  xvii) OF test: Unchanged
  xviii) Pigments production: The microorganism produces water soluble yellow-brown pigments.
  xix) Temperature for growth: 4°–37° C.
  xx) Oxygen demand: Aerobic
  xxi) Formation of acids from the hycarbohydrates:

| glucose | + | maltose | + |
| sucrose | + | galactose | + |
| lactose | − | arabinose | − | xxii) Utilization as a carbon source and an energy source:

| glucose | + | maltose | + |
| sucrose | + | galactose | + |
| lactose | + | arabinose | + | xxiii) The pH value for growth: 5.0–8.5
  xxiv) Halotolerance: 5% NaCl
  xxv) Demand for growth factor: Non
  xxvi) G/C: 66.0%
(3) Corynebacterium sp. N3
  A. Morphological characteristics
    i) Shape and size of a cell: Spherical or rod-shaped cell having size of 0.5–0.8×0.5–2.5 μm
    ii) Polymorphism of a cell: The cell has V-type and Y-type chains.
    iii) Mobility: Non
    iv) Sporulation: Non
    v) Gram stain: Positive
  B. Cultural characteristics
    i) Nutrient agar (30° C., 5 days): Growth is excellent. The shape of the cultured strain is circular. Surface of the cultured strain is slightly rising and smooth. The color of the cultured strain is cream.
    ii) Nutrient agar slant: Growth is excellent. Surface of the cultured strain is smooth. The color of the cultured strain is cream.
    iii) Stab culture: The microorganism grows on the surface of standard agar medium, and does not change gelatin.
    iv) Nutrient broth: The microorganism forms a ring.
  C. Physiological characteristics
    i) Reduction of nitrate: The microorganism does not reduce nitrate.
    ii) Indole production: Negative
    iii) Hydrogen sulfide production: Negative
    iv) VP reaction: Negative
    v) Methyl red reaction: Negative
    vi) Hydrolysis of starch: Negative
    vii) Hydrolysis of gelatin: Positive
    viii) Decomposition of Tween 80: Negative
    ix) Hydrolysis of esculin: Negative
    x) Hydrolysis of casein: Positive
    xi) Egg yolk reaction: Transparentization
    xii) Reaction in the litmus milk: Coagulation
    xiii) Decomposition of arginine: Positive
    xiv) Urease: Negative
    xv) Catalase: Positive
    xvi) Oxidase: Negative
    xvii) OF test: Unchanged
    xviii) Pigments production: The microorganism produces water soluble yellow pigments after long culture.
    xix) Temperature for growth: 4°–35° C.
    xx) Oxygen demand: Aerobic
    xxi) Formation of acids from the carbohydrates:

| glucose | + | (w) | maltose | + |
| sucrose | + | | galactose | + |
| lactose | − | | arabinose | − | xxi) Utilization as a carbon source and an energy source:

| glucose | + | maltose | + |
| sucrose | + | galactose | + |
| lactose | + | arabinose | + | xxiii) The pH value for growth: 4.5–8.5
    xxiv) Halotolerance: 2% NaCl
    xxv) Demand for growth factor: Non
    xxvi) G/C: 73.2%
(4) Cornebacterium sp. N4
  Morphological characteristics
    i) Shape and size of a cell: An irregular rod-shaped cell having size of 0.5–0.6×2.0–5.0 μm
    ii) Polymorphism of a cell: The cell has irregular V-type and Y-type chains.
    iii) Mobility: Non
    iv) Sporulation: Non
    v) Gram stain: Positive
  B. Cultural characteristics
    i) Nutrient agar (30° C., 5 days); Growth is excellent. The shape of the cultured strain is circular. Surface of the cultured strain is rising and slightly coarse. The color of the cultured strain is orange.
    ii) Nutrient agar slant: Growth is excellent. Surface of the cultured strain is smooth. The color of the cultured strain is orange.
    iii) Stab culture: The microorganism grows on the surface of standard agar medium, and does not liquefy gelatin.
    iv) Nutrient broth: The microorganism grows on said medium, and forms a ring.
  C. Physiological characteristics
    i) Reduction of nitrate: The microorganism does not reduce nitrate.

ii) Indole production: Negative
iii) Hydrogen sulfide production: Negative
iv) VP reaction: Negative
v) Methyl red reaction: Negative
vi) Hydrolysis of starch: Positive
vii) Hydrolysis of gelatin: Positive
viii) Decomposition of Tween 80: Positive
ix) Hydrolysis of esculin: Negative
x) Hydrolysis of casein: Positive
xi) Egg yolk reaction: Transparentization
xii) Reaction in the litmus milk: The microorganism produces an alkali.
xiii) Decomposition of arginine dihydrolase: Positive
xiv) Urease: Negative
xv) Catalase: Positive
xvi) Oxidase: Negative
xvii) OF test: Unchanged
xviii) Pigments production: The microorganism does not produce water soluble pigments.
xix) Temperature for growth: 4°–35° C.
xx) Oxygen demand: Aerobic
xxi) Formation of acids from the carbohydrates:

| glucose | + | maltose | + |
| sucrose | + | galactose | + |
| lactose | + | arabinose | + | xxii) Utilization as a carbon source and an energy source:

| glucose | + | maltose | + |
| sucrose | + | galactose | + |
| lactose | + | arabinose | + | xxiii) The pH value for growth: 4.5–8.5
xxiv) Halotolerance: 5% NaCl
xxv) Demand for growth factor: Non
xxvi) G/C: 65.4%

(5) Cornebacterium sp. N5

A. Morphological characteristics
  i) Shape and size of a cell: An irregular rod-shaped cell having size of 0.8–2.0×6.0 μm, and an elongated cell (10 μm).
  ii) Polymorphism of a cell: The cell has V-type and Y-type chains, and is irregularly arranged.
  iii) Mobility: Non
  iv) Sporulation: Non
  v) Gram stain: Positive B. Cultural characteristics is
  i) Nutrient agar (30° C., 5 days): Growth is excellent. The shape of the cultured strain is circular. Surface of the cultured strain is rising and smooth. The color of the cultured strain is cream.
  ii) Nutrient agar slant: Growth is excellent. Surface of the cultured strain is smooth. The color of the cultured strain is cream.
  iii) Stab culture: The microorganism grows on the surface of standard agar medium, and does not change gelatin.
  iv) Nutrient broth: The microorganism grows excellently, and forms a ring.

C. Physiological characteristics
  i) Reduction of nitrate: The microorganism does not reduce nitrate.
  ii) Indole production: Negative
  iii) Hydrogen sulfide production: Negative
  iv) VP reaction: Negative
  v) Methyl red reaction: Negative
  vi) Hydrolysis of starch: Negative
  vii) Hydrolysis of gelatin: Positive
  viii) Decomposition of Tween 80: Positive
  ix) Hydrolysis of esculin: Negative
  x) Hydrolysis of casein: Positive
  xi) Reaction in the litmus milk: The microorganism produces an alkali.
  xii) Decomposition of arginine dihydrolase: Positive
  xiii) Vrease: Negative
  xiv) Catalase: Positive
  xv) Oxidase: Negative
  xvi) OF test: Unchanged
  xvii) Pigments production: The microorganism produce water soluble yello pigments after long culture.
  xviii) Temperature for growth: 4°–35° C.
  xix) Oxygen demand: Aerobic
  xxi) Formation of acids from the carbohydrates:

| glucose | + | (W) | maltose | + |
| sucrose | + | (W) | galactose | + |
| lactose | − |     | arabinose | − | xxi) Utilization as a carbon source and an energy source:

| glucose | + | maltose | + |
| sucrose | + | galactose | + |
| lactose | + | arabinose | + | xxii) The pH value for growth: 4.5–8.5
xxiii) Halotolerance: 4% NaCl
xxiv) Demand for growth factor: Non The aforesaid characteristics of these strains were referred to "Burgy's Manual Systematic Bacteriology" (8th edition). The results show that these strains belong to Corynebacterium.

xxvi) G/C: 71.5%

The aforesaid characteristics of these strains were referred to "Burgy's Manual Systematic Bacteriology" (8th edition). The results show that these strains belong to Corynebacterium.

These strains are named as Cornebacterium sp. N1, Corynebacterium sp N2, Cornebacterium sp. N3, Cornebacterium sp. N4 and cornebacterium sp. N5. These Cornebacterium sp. N1, N2, N3, N4 and N5 are deposited under the Budapest Treaty in the National Institute of Bioscience and Human Technology (Japan) having an adress of 1–3, Higashi 1-chome, Tsukuba-shi, Ibaraki-ken, 305 JAPAN as FERM BP-5967, FERM BP-5968, FERM BP-5639, FERM BP-5969 and FERM BP-5970, respectively. These deposits were each accepted by the depository as of Sep. 12, 1995. The present invention includes all the variants having decomposiblity for ethynol amines, said variants being prepared by varying the aforesaid strains by means of natural or artificial methods.

In order to decompose ethanolamines by means of the aforementioned strains, said strains should be contacted with ethanolamines. Although special conditions are unnecessary for the decomposition of ethanolamines, these strains may be contacted with a system which comprises ethanolamines as well as another ingredient, such as an inorganic nitrogen source (e.g. ammonium nitrate and the like), a phosphorus source (e.g. potassium phosphate and the like), an inorganic salt (e.g. magnesium salt, iron salt and the like), and an organic growth factor (e.g. yeast extract, peptone and the like). The culture of these strains with ethanolamines may be continued under aerobic condition (pH 6.0–8.0) at 15°–35° C., preferably 20°–30° C. so that ethanolamines will sufficiently be decomposed.

Concentration of ethanolamines in the waste fluid to be treated can be varied over a wide range (e.g. 0–4%, preferably 0–2%). High concentration of ethanolamines in the waste fluid to be treated can efficiently be decomposed.

Ethanolamines can completely be decomposed by culturing the strains with ethanolamines for 7–10 days under the aforementioned conditions.

The aforesaid waste fluid comprises various substances other than ethanolamines. Therefore, the substances which hinder the aforementioned treatment with the aforesaid microorganism may be removed from the waste fluid before said treatment. It is preferable to adopt a suitable pretreatment for each waste fluid because the compositions of the aforesaid waste fluids vary depending on the kinds of the waste fluids. An ordinary pretreatment consists of a process for filtering sludges, such as metal components in the waste fluids, and a process for physicochemically treating a preservative, a rust preventative and the like in the filtrate of the waste fluids. These processes may be continuous or batch-wise. In addition, it is preferable to adopt a suitable posttreatment in order to remove the nitrogen compounds formed by the decomposition of ethanolamines during the aforesaid treatment with the microorganisms, residual microorganisms and dead bodies thereof from the treated waste fluids. As an ordinary post-treatment, the present invention makes use of an active sludge treatment, or a biological or physicochemical treatment of the denitrification products and a process for filtering the agglomerated precipitate of the remained microorganisms. According to the present invention, ethanolamines in the waste fluids can completely be decomposed and removed form the waste fluids by the aforementioned processes including the pretreatment and the post-treatment.

Furthermore, the present invention provides a process for treating an ammoniacal nitrogen in the waste fluid treated by the aforesaid microorganisms which comprises (i) removing the ingredients which inhibit the treatment by microorganisms, such as a preservative, a rust preventative and the like from the waste fluid, (ii) supplying the pretreated waste fluid to a semi-closed biological treatment tank equipped with an inlet and an outlet for a gas, (iii) adding the aforesaid microorganisms to said tank to decompose ethanolamines in the waste fluid into an ammonium ion, (iv) adding an alkali to said tank to produce free ammonia at a pH of more than 10, (v) discharging the free ammonia as an ammonia gas through the outlet of said tank, and (vi) subjecting the waste fluid in said tank to a post-treatment selected from the group consisting of agglomerative precipitation and neutralization. A degree of decomposition of ethanolamines in the waste fluid can be determined by measuring an increase of ammonium ion concentration or a decrease of ethanolamines concentration in the waste fluid. Preferably, the alkali may be added to the waste fluid treated by the microorganism when the ammonium ion concentration becomes more than 800 ppm or the ethanolamines concentration becomes less than 50 ppm.

According to the present invention, the ammonia stripping treatment may automatically be followed after an automatic determination of the increase of ammonium ion concentration or the decrease of ethanolamines concentration in the waste fluid treated by the microorganisms.

In order to carry out the aforesaid process for treating an ammoniacal nitrogen in the waste fluid treated by the microorganisms, it is preferable to employ an apparatus for treating an ammoniacal nitrogen in the waste fluid treated by the aforesaid microorganisms which comprises (i) a pretreatment tank for removing ingredients which inhibit the treatment by said microorganisms, such as a preservative, a rust preventative and the like from the waste fluid, and (ii) a semi-closed biological treatment tank equipped with an inlet for introducing the pretreated waste fluid, an inlet for introducing a blowing gas through said waste fluid, an outlet for discharging said blowing gas and any generated gas which is connected with an absorption tower for ammonia gas, an inlet for introducing an alkali, a detector for detecting concentrations of ingredients in said waste fluid, and an outlet for discharging said waste fluid in order to subject said waste fluid to a post-treatment including an agglomerative precipitation and a neutralization.

The detector for detecting concentrations of ingredients in the waste fluid consists of a detecting means for detecting a completion of the biological treatment of the waste fluid and a detecting means for detecting pH of the waste fluid. The detecting means for detecting a completion of the biological treatment of the waste fluid may be a detector for determining concentrations of the ingredients in the waste fluid, such as an ion electrode, an ion chromatography and the like.

In order to adjust the pH value of the waste fluid to 10–13, the aforementioned apparatus according to the present invention may be equipped with a means for adding the alkali to the waste fluid when the detecting means for detecting a completion of the biological treatment of the waste fluid detects said completion, and a means for stopping said addition of the alkali when the pH value of the waste fluid reaches the defined upper limit.

DESCRIPTION OF THE SPECIFIC EMBODIMENTS

Figure 1:
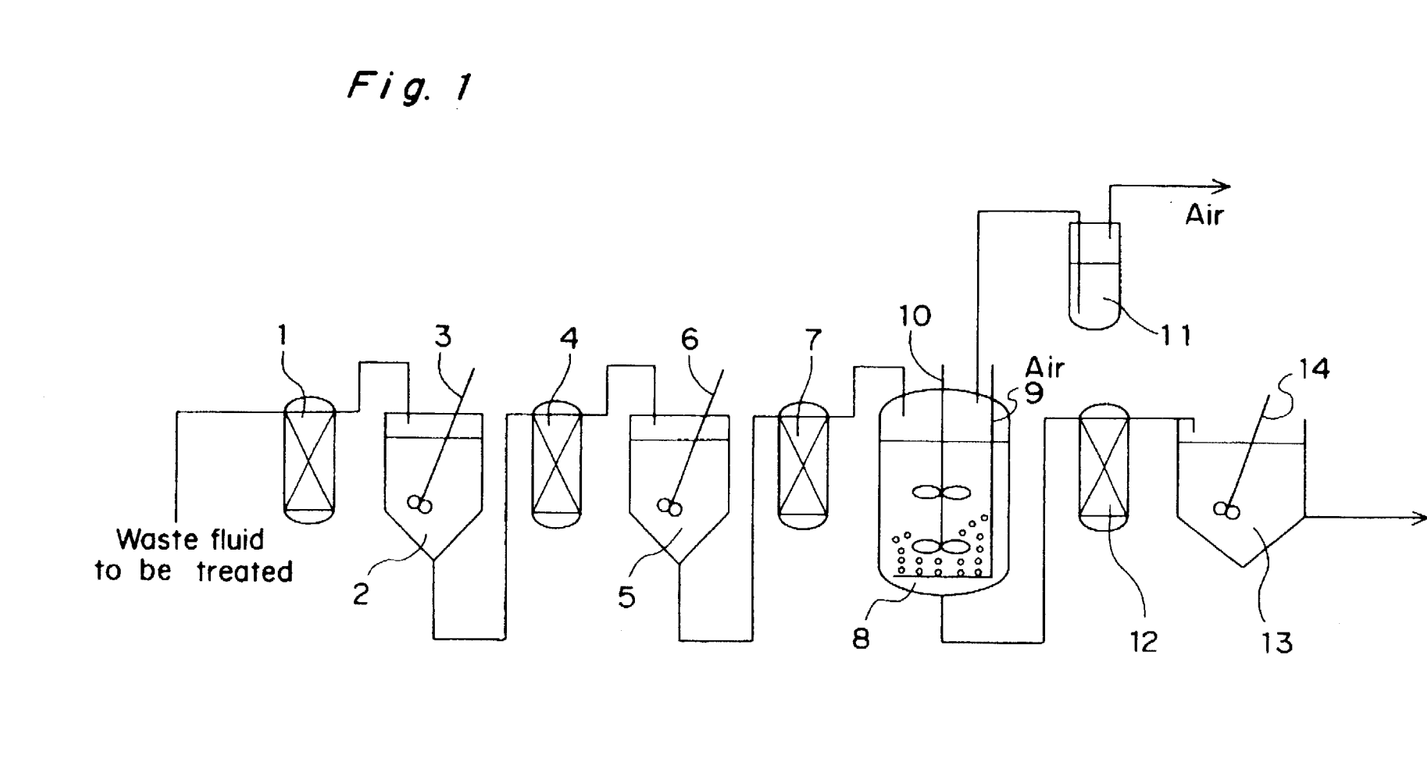
FIG. 1 is a schematic flow chart which shows a process for treating a waste fluid containing ethanolamines by means of the microorganisms according to the present invention.

One embodiment of the present invention will be illustrated on the basis of FIG. 1. FIG. 1 is a schematic flow chart which shows a process for treating the waste fluid containing ethanolamines by means of the microorganisms according to the present invention.

The waste fluid containing ethanolamines (especially triethanolamine and diethanolamine) is supplied to the alkali tank (2) after passing thorough the filter (1) to remove a metal sludge and the like. In order to remove any preservative, a rust preventative and the like which inhibit the treatment of the waste fluid by means of the microorganisms, an alkaline solution is poured into the alkali tank (2) under agitation of the waste fluid by means of the agitator (3) to precipitate the metal salts formed. The treated waste fluid is supplied to a neutralization tank (5) after passing through a filter (4) to remove the precipitate. An acid solution is poured into the neutralization tank (5) under agitation of the waste fluid by means of agitator (6) to neutralize the alkaline ingredients, and the reaction products are removed by means of the filter (7).

The neutralized waste fluid is supplied to the treating tank with microorganisms (8) to mix or contact the fluid with one or more of the aforementioned microorganisms. The nutrients for the microorganisms are poured into the tank (8), and air supplied from the air inlet (9) is introduced into the tank (8) through the bottom thereof under agitation of the waste fluid by means of agitator (10) at a controlled temperature. After a certain period, ethanolamines (especially triethanolamine and diethanolamine) in the waste fluid are decomposed.

In order to treat the nitrogen compounds included in the decomposition products of ethanolamines by means of ammonium stripping method, an alkaline solution is poured into tank (8) under agitation of the waste fluid to exhaust ammonium ion of the nitrogen compounds as ammonia gas. The ammonia gas is supplied to the absorption tank for ammonia (11) by means of the air supplied through the bottom of the tank (8).

An acid solution in the tank (11) absorbs the ammonia gas, and only harmless air is exhausted to the atmosphere.

An inorganic coagulant is poured into the waste fluid remaining in tank (8) under the agitation of the waste fluid in order to agglutinate the microorganisms and dead bodies thereof. In addition, a polymer coagulant is poured into tank (8) under agitation of the waste fluid in order to grow the agglutinates. The treated waste fluid is supplied to the drainage tank (13) after passing through the filter (12) to remove the agglomerated precipitate. An acid solution is poured into tank (13) under agitation of the treated waste fluid in order to neutralize said fluid. The neutralized waste fluid is discharged.

The aforementioned embodiment of the present invention will be illustrated more concretely.

The aqueous waste fluid of a machining oil used in a factory is supplied to alkali tank (2) after passing through filter (1) to remove sludge, such as metal powder and the like. A certain amount of slaked lime slurry is poured into alkali tank (2), and the waste fluid is mixed with slaked lime slurry by means of agitator (3), wherein the pH of the mixture is adjusted to 12–13. In the course of this process, the preservative and the rust preventative (e.g. carboxylic acids, medium fatty acids and the like) precipitate as a calcium salt, and heavy metal ions separate out as a hydroxide. In addition, an anionic polymer coagulant is added into alkali tank (2) under agitation to coagulate the precipitated calcium salts and hydroxides.

The treated waste fluid is supplied to neutralization tank (5) after passing through filter (4) to remove the aforesaid precipitates. A certain amount of dilute sulfuric acid is poured into neutralization tank (5), and the waste fluid is mixed with dilute sulfuric acid by means of agitator (6), wherein pH of the mixture is adjusted to 6–8. The precipitated salts formed by neutralization is removed from the waste fluid by means of filter (7).

The waste fluid supplied to the treating tank with microorganism (8) contains triethanolamine (10,000 ppm). Cornebacterium sp. N2 and nutrients (an aqueous solution comprising potassium chloride, potassium dihydrogen phosphate, magnesium sulfate, sodium citrate and the like) are poured into tank (8), and mixed with the waste fluid by means of agitator (10). Air is supplied from the air inlet (9), and introduced into the waste fluid through the bottom of the tank (8). The waste fluid in the tank (8) is treated with the microorganism at 25° C.

Figure 2:
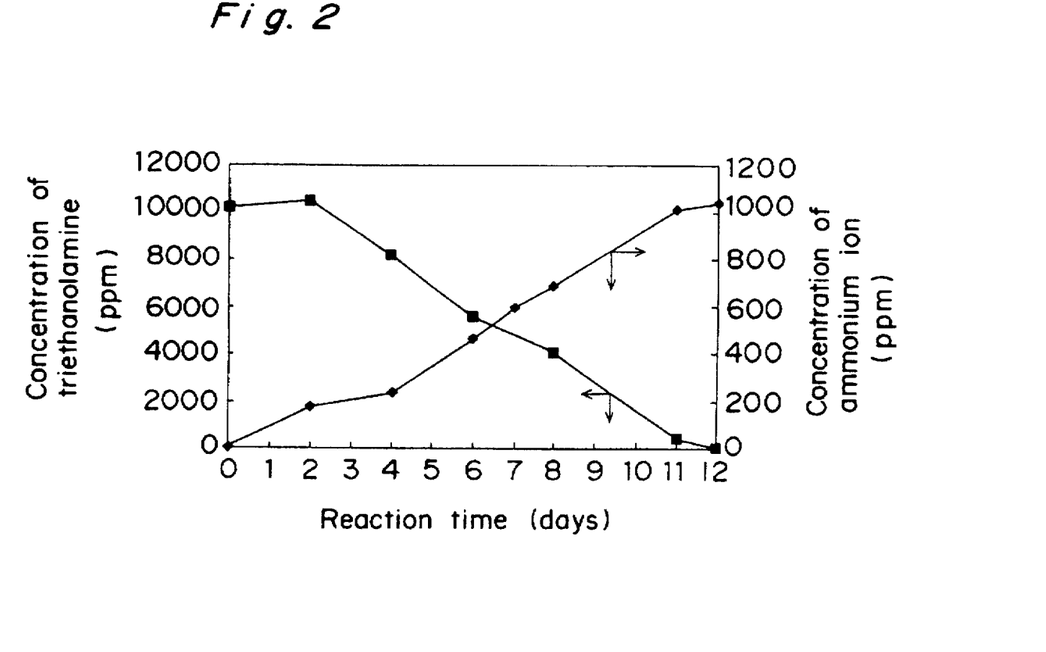
FIG. 2 shows the concentration changes of triethanolamine and ammonium ion in the waste fluid with the passage of time.

FIG. 2 shows the concentration changes of triethanolamine and ammonium ion which is a decomposition product of triethanolamine in the waste fluid with the passage of time. As can be seen from FIG. 2, triethanolamine is perfectly decomposed after 12 days.

In the case where the waste fluid in the tank (8) contains triethanolamine (2,600 ppm) and diethanolamine (930 ppm), cornebacterium sp. N2 and N3 and the nutrients (an aqueous solution comprising potassium chloride, potassium dihydrogen phosphate, magnesium sulfate, sodium citrate and the like) are poured into tank (8), and mixed with the waste fluid by means of agitator (10). Air is supplied from the air inlet (9), and introduced into the waste fluid through the bottom of tank (8). The waste fluid in tank (8) is treated with microorganisms at 25° C.

Figure 3:
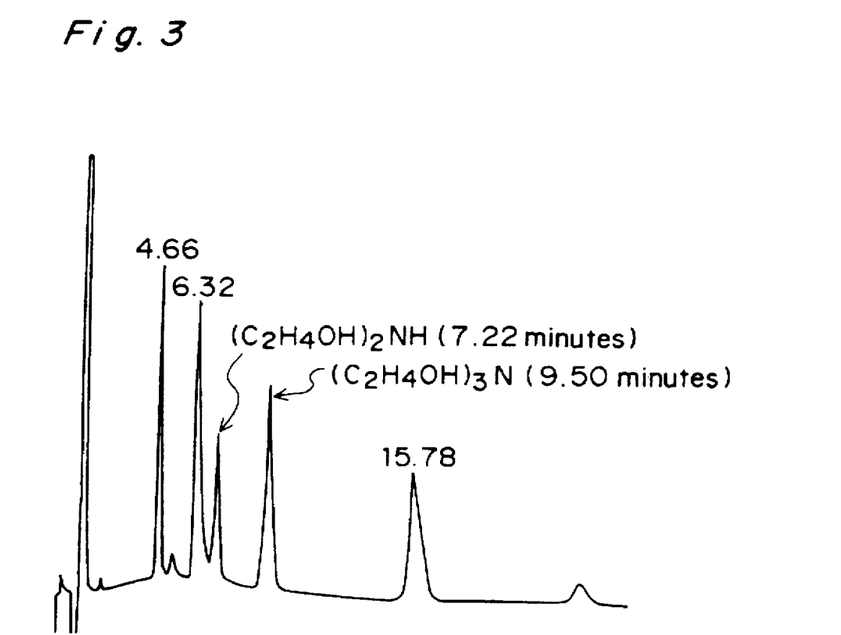
FIG. 3 shows the ion chromatograms of the waste fluid at the starting time.
Figure 4:
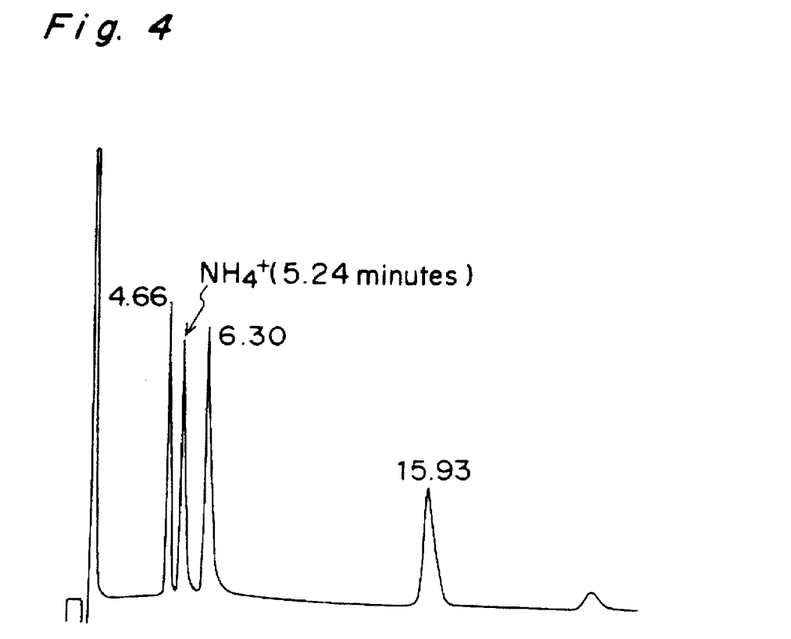
FIG. 4 shows the ion chromatogram of the waste fluid after 7 days.

The ion chromatograms of the waste fluid at the starting time and after 7 days are shown in FIG. 3 and FIG. 4 respectively. As can be seen from these figures, triethanolamine and diethanolamine are completely decomposed, and ammonium ion, which is one of the decomposition products of said ethanolamines, is formed after 7 days.

After the decomposition of ethanolamines in the waste fluid, a certain amount of aqueous solution of sodium hydroxide is poured into tank (8) to adjust pH of the waste fluid to 12–13. The ammonium ion formed by the microorganism treatment is introduced as ammonia gas into the absorption tank for ammonia (11) by means of the air pressure in the tank (8). The aqueous solution of dilute sulfuric acid in the tank (11) absorbs the ammonia gas, and only harmless air is exhausted to the atmosphere.

Polyaluminum chloride (an inorganic coagulant) is added to the waste fluid remaining in tank (8) under agitation of the waste fluid in order to agglutinate the microorganism and the dead bodies thereof. In addition, an anionic polymer coagulant is added to the tank (8) under the agitation of the waste fluid in order to grow the agglutinates. The treated waste fluid is supplied to drainage tank (13) after passing through filter (12) to remove the agglomerated precipitate. The aqueous solution of dilute sulfuric acid is poured into tank (13) under agitation of the treated waste fluid by means of agitator (14) in order to neutralize said fluid (pH: ca.7). The neutralized waste fluid is discharged.

Figure 5:
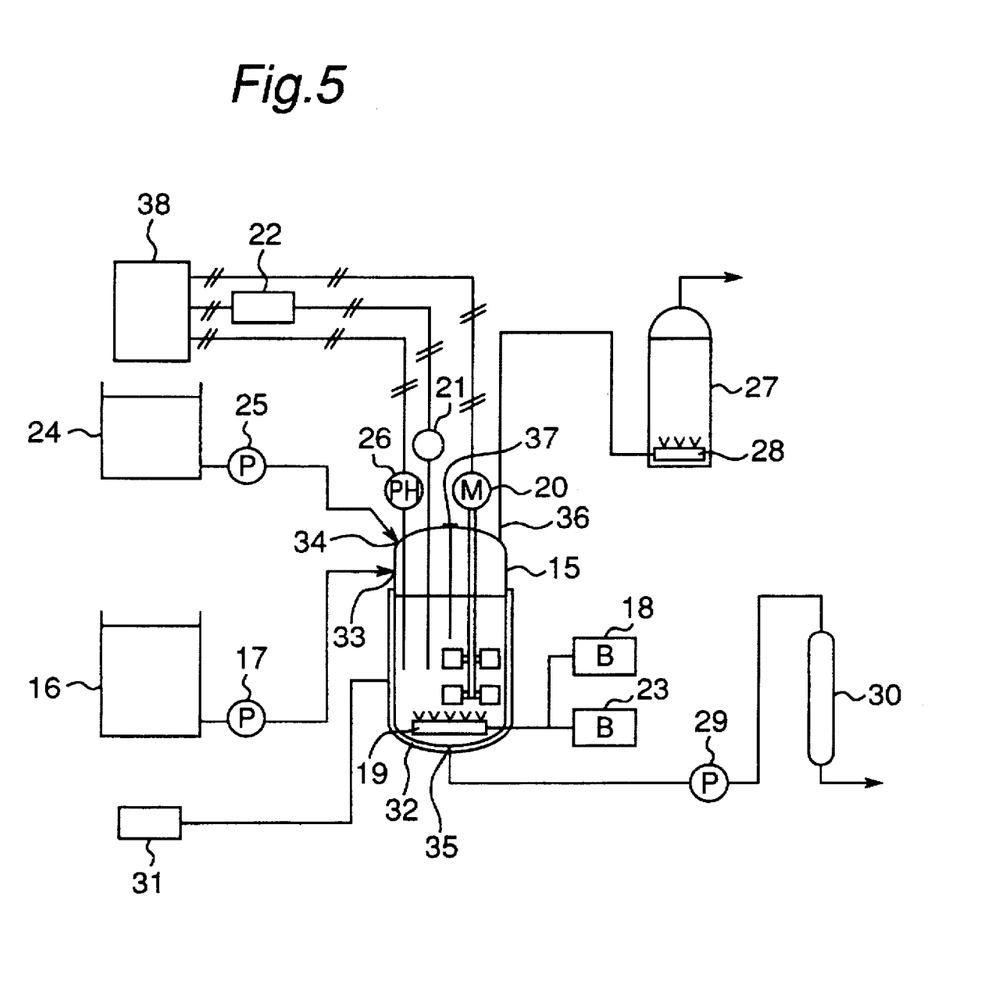
FIG. 5 is another schematic flow chart which shows a process for treating a waste fluid containing ethanolamines by means of the microorganisms according to the present invention.

Another embodiment of the present invention will be illustrated on the basis of FIG. 5. FIG. 5 is a schematic flow chart which shows a process for treating a waste fluid containing ethanolamines by means of microorganisms suitable for decomposing ethanolamines. Preservatives, rust preventatives and the like which inhibit the treatment of the waste fluid by the biological method are removed in pretreatment tank (16) which is connected with reaction tank (15). The pretreated waste fluid is supplied to tank (15) by way of pump (17). An alkali (caustic soda) is stored in alkali tank (24) in order to separate ammonia gas in tank (15) which is connected with alkali tank (24). Caustic soda is supplied to tank (15) by way of pump (25). Tank (15) is equipped with inlet (33) for the pretreated waste fluid, inlet (34) for caustic soda and inlet (37) for microorganisms which are cultured in an incubator (not shown). The bottom of tank (15) is equipped with air diffusion pipe (19) for aerating the waste fluid in the tank (15). Air diffusion pipe (19) is connected to a small-sized blower (18) and a large-sized blower (23) through which small amounts to large amounts of air can be supplied to the tank (15). The top of the tank (15) is equipped with outlet (36) for the supplied air and any produced gas (ammonia gas) in tank (15) and agitator (20) for agitating the waste fluid in tank (15).

Tank (15) is equipped with ion electrode (21) which detects an electrical conductance of ammonium ion in the waste fluid and a measuring device (ammonium ion meter) (22) which determines the concentration of ammonium ion based on the output of the ion electrode. The concentration signal from the measuring device (22) is imputed to the controlling device (38). Tank (15) is equipped with measuring device (pH meter) (26) for measuring pH of the waste fluid, and the pH signal from the measuring device is imputed to the controlling device (38). The controlling device (38) starts an operation of the pump (25) for caustic soda according to the output signal from measuring device (22) for ammonium ion concentration in order to supply caustic soda to tank (15) and stops the operation of pump (25) for caustic soda according to the upper limit of the output signal from pH meter in order to stop the supply of caustic soda.

The bottom of tank (15) is equipped with outlet (35) for discharging the waste fluid. Outlet (35) is connected to post-treatment systems (not shown), such as a system for agglomerative precipitation treatment, a system for neutralization treatment and the like, by way of pump (29) and filter (30). Outlet (36) is connected to the absorption tower for ammonia (27) which contains dilute sulfuric acid by way of air diffusion pipe (28). Reaction tank (15) is equipped with the water cooling jacket (32) through which warm or cold water circulates according to the temperature control unit (31).

The function of the aforementioned apparatus will be illustrated more concretely.

The preservative, the rust preventative and the like, which inhibit the treatment of the waste fluid by the microorganisms, are removed in pretreatment tank (16). The pretreated waste fluid is supplied to reaction tank (15) by way of pump (17). Cornebacterium sp. N having decomposability for ethanolamines are introduced into reaction tank (15), and air (0.2–0.3 m$^3$/min) supplied from small-sized blower (18) is flowed into reaction tank (15) by way of air diffusion pipe (19) arranged in the bottom of reaction tank (15). A biological reaction is carried out under agitation by means of agitator (20), and ethanolamines in the waste fluid are decomposed after 7–10 days. The waste fluid subjected to the biological treatment contains about 1,000 ppm of ammonium ion which is a decomposition product of ethanolamines.

When the concentration of ammonium ion becomes more than a preset value, ion electrode (21) arranged in the upper part of reaction tank (1) outputs a signal which is transmitted to measuring device (22) by way of detector (21). From a viewpoint of a reacting weight and a reaction time, an effective preset concentration of ammonium ion is, for example, about 800 ppm. When the signal is transmitted to measuring device (22), said device sends an end signal to the controlling device (38). When the controlling device (38) receives the end signal, it stops the small-sized blower (18) and starts operation of the large-sized blower (23) to flow air (10–13 m$^3$/min) into reaction tank (15) by way of air diffusion pipe (19).

Caustic soda stored in alkali tank (24) is poured into reaction tank (15) by way of pump (25) which is controlled by the controlling device (38).

The measuring device (26) determines the pH of the waste fluid in reaction tank (15) and outputs a signal concerning the pH value to controlling device (38) which operates pump (25) in such a way that the pH of the waste fluid in reaction tank (15) is adjusted to 10–13. Under these conditions, ammonium ion in the waste fluid changes to free ammonia which becomes ammonia gas by diffusion in the flowed air. During the above process, agitator (20) operates successively.

The air which contains the diffused ammonia gas is supplied to air diffusion pipe (28) arranged in the absorption tower for ammonia (27) through outlet (36) arranged in the upper part of reaction tank (15). The ammonia gas in the air supplied to the air diffusion pipe (28) reacts with dilute sulfuric acid stored in the absorption tower (27) to form ammonium sulfate which remains in the absorption tower (27). The air from which ammonia gas is removed is harmless and may be discharged into the atmosphere.

The aforementioned ammonia stripping treatment may be stopped when the concentration of ammonium ion in the waste fluid becomes less than 50 ppm. The concentration of ammonium ion in the waste fluid can be determined by means of ion electrode (21) and the measuring device (22). The treated waste fluid from which ammonia is removed in reaction tank (15) is discharged through outlet (35) by means of pump (29). In order to separate the microorganisms, dead bodies thereof and other materials in the waste fluid, a polymer flocculating agent may be added to reaction tank (15) to agglomerate and precipitate these materials in the waste fluid. The waste fluid containing the precipitates is passed through the filter (30), and the filtrate is subjected to a neutralization treatment. The neutralized waste fluid can be discharged.

As a means to detect completion of the biological treatment of the waste fluid, ion chromatography may be employed in place of the ion electrode (21). In this case, the waste fluid treated with the microorganisms may be subjected to ammonia stripping treatment when the total concentration of triethanolamine and diethanolamine which are strong toxic amines becomes less than 50 ppm. In comparison with the ion electrode, the detector of ion chromatography is expensive and makes a continuous measurement impossible.

However, the strong toxic ethanolamines in the waste fluid can be decreased with certainty because the concentrations of said ethanolamines can be determined directly by means of ion chromatography.

Although equipment such as a precipitation tank and the like are unnecessary in the case where flocculation and precipitation treatment is carried out in reaction tank (15) in order to separate the microorganisms, dead bodies thereof and other materials, the next biological treatment of the waste fluid cannot be conducted during the precipitation treatment (1–2 days). Therefore, another precipitation tank may be arranged according to the amounts of the waste fluid to be treated.

Temperature of the waste fluid in the reaction tank (15) can be adjusted by means of the water cooling jacket (32). The biological reaction in reaction tank (15) may be accelerated by warming or cooling the waste fluid to 25° C. In the process for separating ammonia gas, high temperature may be preferred to separate ammonia gas effectively. However, reaction rate of ammonia and sulfuric acid in the absorption tower (27) decreases at more than 100° C. Therefore, the separation and absorption of ammonia gas may be accelerated by warming or cooling the waste fluid to 50° C.

If a hot vapor supplied from a boiler and the like arranged in the neighborhood can be utilized, the hot vapor (more than 100° C.) may be supplied to reaction tank (15) to separate ammonia gas, and ammonia gas exhausted from outlet (36) may be supplied to absorption tower (27) after cooling said gas to 50° C. by means of a heat exchanger.

By utilizing cornebacterium sp. N according to the present invention, massive amounts of ethanolamine containing waste fluid discharged from a metal processing factory and the like can effectively be treated without causing environmental pollution.

According to the present invention, it is possible to treat the waste fluids, such as factory wastes and the like which contain ethanolamines in a small-scale manner, because the biological treatment of the waste fluid and the ammonia stripping treatment can successively be carried out in a biological reaction tank. The apparatus according to the present invention can readily be installed, and the initial and running costs, such as maintenance of said apparatus are inexpensive.

Furthermore, according to the present invention, the completion on the biological treatment of the waste fluid can be determined by measuring an increase of the ammonium ion concentration in the waste fluid or a decrease of the total concentration of ethanolamines in the waste fluid, and said biological treatment is automatically followed by the next process wherein the pH value of the waste fluid can automatically be adjusted to a preset value by automatically, stopping the supply of an alkali according to a detected pH value. Therefore, waste fluid can be treated stably and effectively by means of the apparatus according to the present invention, said apparatus being easily manageable and operable.

EXAMPLES

The following examples are offered by way of illustration and not by way of limitation.

Example 1

One hundred milliliters of the culture medium (pH: 7.0) which comprises triethanolamine (1%), potassium dihydrogen phosphate (0.1%), $MgSO_4 \cdot 7H_2O$ (0.02%) and the yeast extract (0.1%) was poured into the vibrating flask (500 ml). The culture medium the flask was subjected to the ordinary sterilization treatment. A unit of platinum wire loop of each strain of Cornebacterium sp. N1–N5 was inoculated into the sterilized culture medium. The inoculated culture medium with said strain was subjected to the vibrating culture at 20° C. The concentration of triethanolamine in the culture medium was determined with the passage of time. The relationship between the concentration of triethanolamine and the culture time is shown in FIG. 6.

Figure 6:
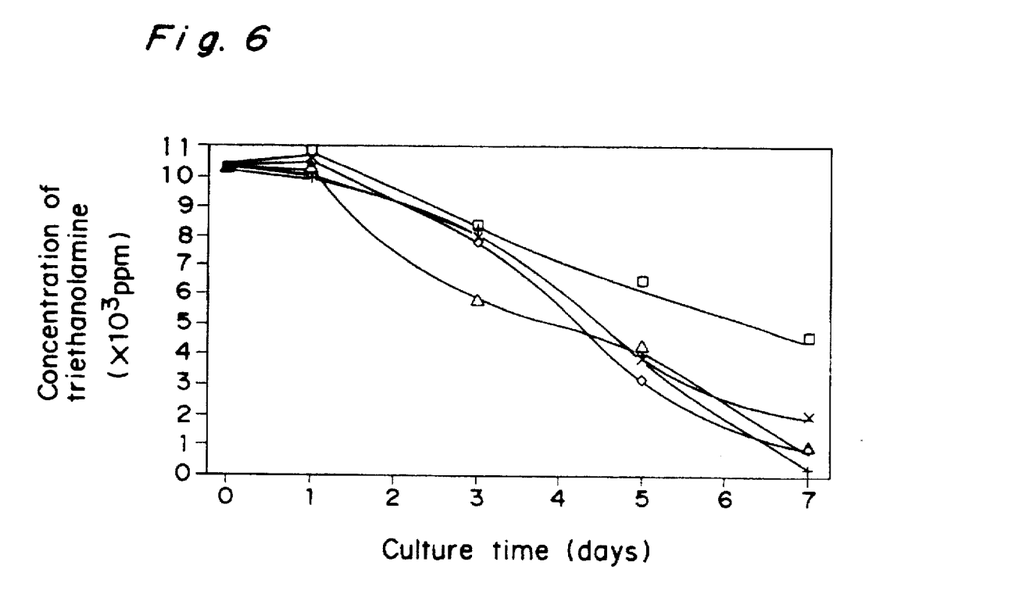
FIG. 6 shows the relationship between the concentration of triethanolamine in the waste fluid and the culture time in Example 1.

The legends appeared in FIG. 6 are as follow:

"☐" . . . Cornebacterium sp. N1

"+" . . . Cornebacterium sp. N2

"◇" . . . Cornebacterium sp. N3

"△" . . . Cornebacterium sp. N4

"x" . . . Cornebacterium sp. N5

As is obvious from FIG. 6, the concentration of triethanolamine is decreased with the growth of the strains according to the present invention.

Example 2

The pH value of the waste fluid of the machining oil which contains triethanolamine was adjusted to 2–3 by adding sulfuric acid to said waste fluid, and the precipitated ingredients were removed by filtration. One percent of active carbon was added to the filtrate and the mixture was agitated for 30 minutes. The active carbon was removed from the filtrate by filtration, and pH of said filtrate was adjusted to 7 by adding slaked lime. The pretreated waste fluid (3000 ml) was poured into the fermenter, and potassium dihydrogen phosphate (300 mg) and $MgSO_4 \cdot 7H_2O$ (60 mg) were added to the waste fluid in the fermenter. In addition, one milliliter of each strain of Cornebacterium sp. N1–N5 which were grown on the triethanolamine containing culture medium as described in Example 1 was inoculated into the waste fluid in the fermenter and cultured under the following conditions:

Airing amounts . . . 1 liter/minute

Agitation rate . . . 60 rotations/minute

Culture temperature . . . 25° C.

Figure 7:
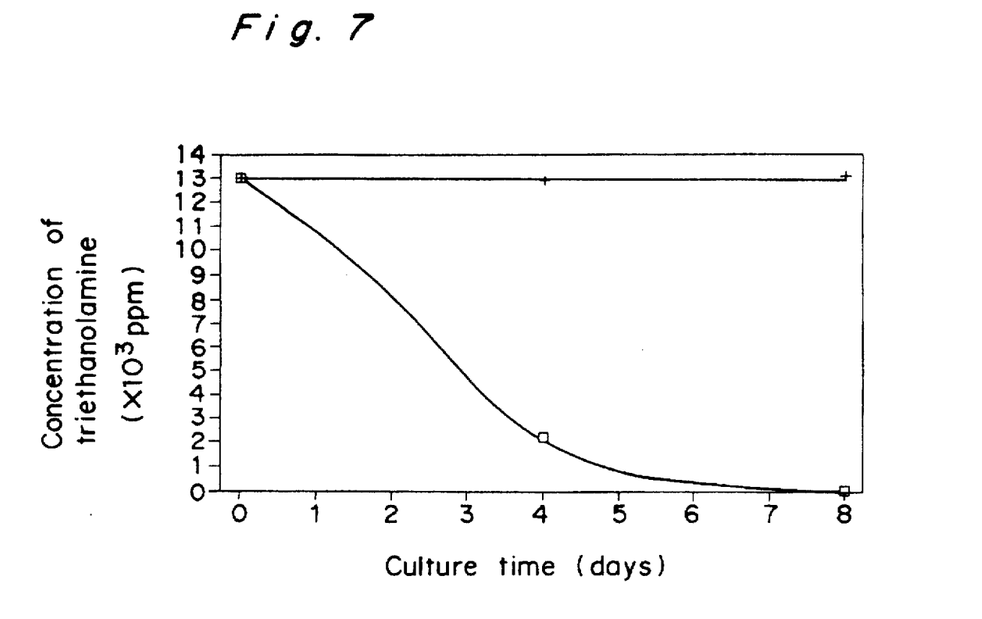
FIG. 7 shows the relationship between the concentration of triethanolamine in the waste fluid and the culture time in Example 2.

The relationship between the concentration of triethanolamine and the culture time is shown in FIG. 7.

The legends appeared in FIG. 7 are as follows:

"☐" . . . Cornebacterium sp. N1–N5

"+" . . . Control

As is obvious from FIG. 7, the concentration of triethanolamine is decreased with the growth of the strains according to the present invention, and triethanolamine is completely decomposed after 7 days of the culture.

Example 3

The pH value of the waste fluid of the machining oil which contains triethanolamine was adjusted to 2–3 by adding sulfuric acid to said waste fluid, and the precipitated ingredients were removed by filtration. One percent of active carbon was added to the filtrate and the mixture was agitated for 30 minutes. The active carbon was removed from the filtrate by filtration, and pH of said filtrate was adjusted to 7 by adding slaked lime. The pretreated waste fluid (3000 ml) was poured into the fermenter, and potassium dihydrogen phosphate (300 mg) and $MgSO_4 \cdot 7H_2O$ (60 mg) were added to the waste fluid in the fermenter. In addition, one milliliter of the strain of Cornebacterium sp. N3 which was grown on the triethanolamine containing culture medium as described in Example 1 was inoculated into the waste fluid in the fermenter and cultured under the following conditions:

Airing amounts . . . 1 liter/minute

Agitation rate . . . 60 rotations/minutes

Culture temperature . . . 25° C.

Figure 8:
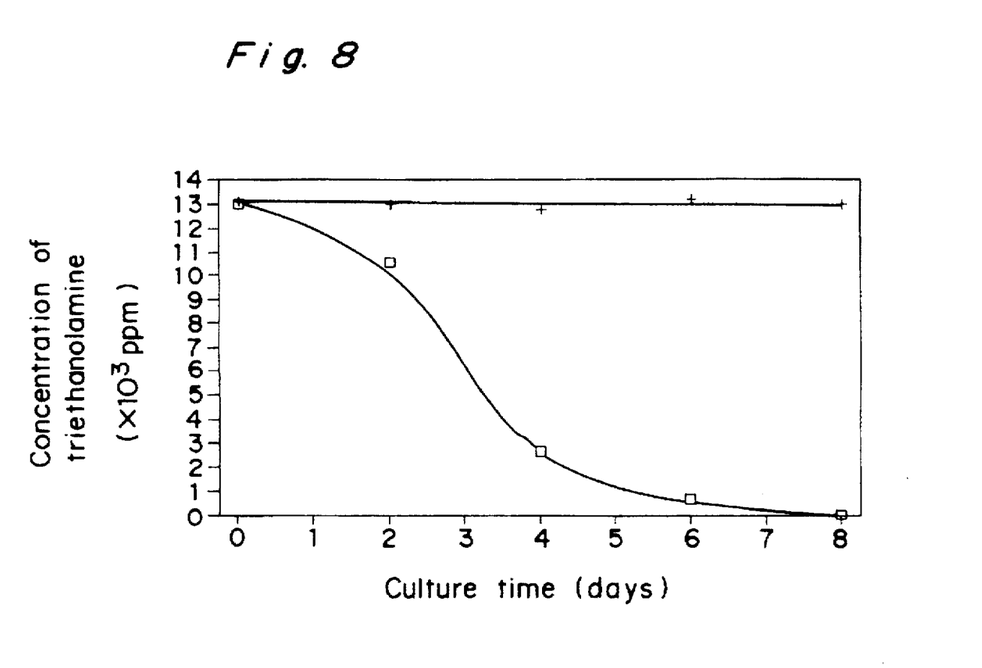
FIG. 8 shows the relationship between the concentration of triethanolamine in the waste fluid and the culture time in Example 3.

The relationship between the concentration of triethanolamine and the culture time is shown in FIG. 8.

The legends appeared in FIG. 8 are as follows:

"☐" . . . Cornebacterium sp. N3

"+" . . . Control

As is obvious from FIG. 8, the concentration of triethanolamine is decreased with the growth of the strain according to the present invention, and triethanolamine is completely decomposed after 8 days of the culture.

Example 4

The pH value of the waste fluid of the machining oil which contains triethanolamine was adjusted to 2–3 by adding sulfuric acid to said waste fluid, and the precipitated ingredients were removed by filtration. One percent of active carbon was added to the filtrate and the mixture was agitated for 30 minutes. The active carbon was removed from the filtrate by filtration, and pH of said filtrate was adjusted to 7 by adding slaked lime. The pretreated waste fluid (3000 ml) was poured into the fermenter, and potassium dihydrogen phosphate (300 mg) and $MgSO_4 \cdot 7H_2O$ (60 mg) were added to the waste fluid in the fermenter. In addition, one milliliter of the strain of cornebacterium sp. N2 which was grown on the triethanolamine containing culture medium as described in Example 1 was inoculated into the waste fluid in the fermenter and cultured under the following conditions:

Airing amounts . . . 1 liter/minute

Agitation rate . . . 60 rotations/minutes

Culture temperature . . . 25° C.

Figure 9:
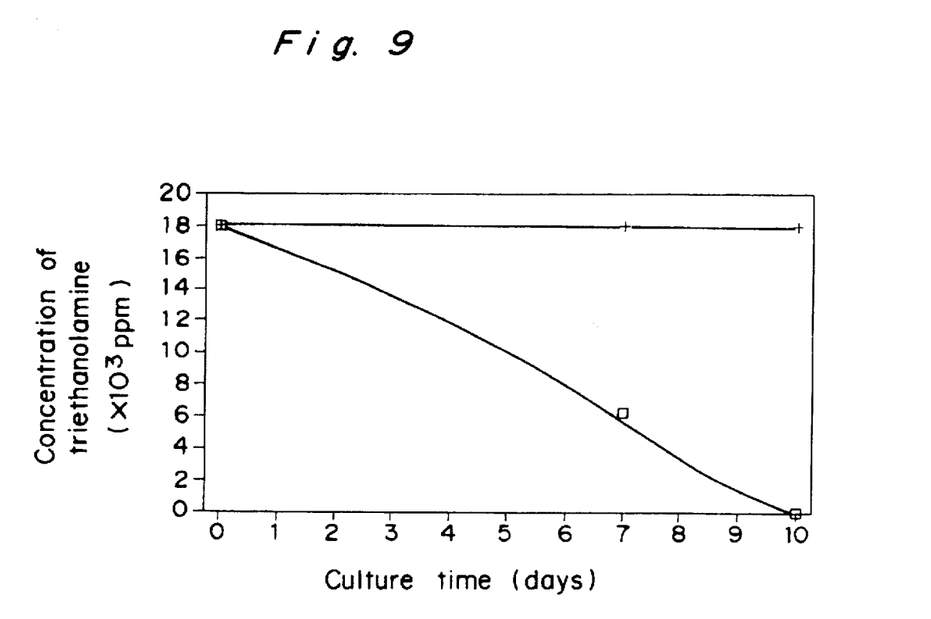
FIG. 9 shows the relationship between the concentration of triethanolamine in the waste fluid and the culture time in Example 4.

The relationship between the concentration of triethanolamine and the culture time is shown in FIG. 9.

The legends appeared in FIG. 9 are as follows:

"☐" . . . Cornebacterium sp. N2

"+" . . . Control

As is obvious from FIG. 9, the concentration of triethanolamine is decreased with the growth of the strain according to the present invention, and triethanolamine is completely decomposed after 10 days of the culture.

Example 5

One hundred milliliters of the culture medium which contains diethanolamine (0.3%), potassium dihydrogen phosphate (0.1%), $MgSO_4 \cdot 7H_2O$ (0.02%) and the yeast extract (0.1%) was poured into the vibrating flask (500 ml). The culture medium in the flask was subjected to the ordinary sterilization treatment. One milliliter of the strain of Corynebacterium N2 or N3 which was grown on the triethanolamine containing culture medium as described in Example 1 was inoculated into the culture medium in the flask and culture at 25° C. under agitation. In any case of the strains, diethanolamine (3000 ppm) was completely decomposed after 7 days of the culture.

Example 6

The pH value of the waste fluid of the machining oil which contains triethanolamine and diethanolamine was adjusted to 12 by adding slaked lime to said waste fluid, and the precipitated ingredients were removed by filtration. The pH value of the filtrate was adjusted to 1 by adding sulfured acid to said filtrate. One hundred milliliters of the filtrate was poured into the vibrating flask, and potassium dihydrogen phosphate (10 mg) and $MgSO_4 \cdot 7H_2O$ (2 mg) were added to the filtrate in the flask. One milliliter of the strain of cornebacterium sp. N2 which was grown on the triethanolamine containing culture medium as described in Example 1 was inoculated into the filtrate in the flask and cultured at 25° C. under agitation.

Figure 10:
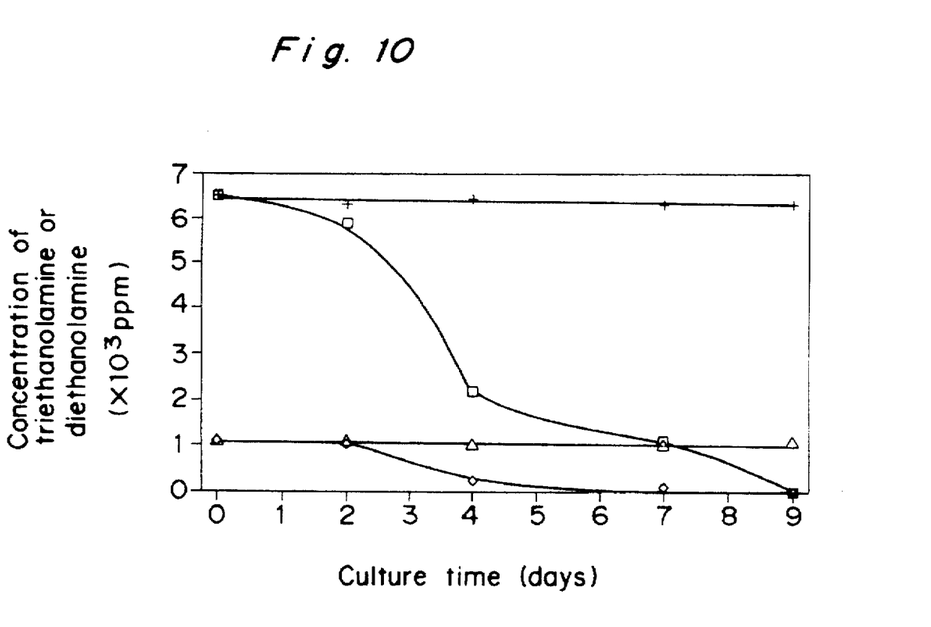
FIG. 10 shows the relationship between the concentration of triethanolamine or diethanolamine in the waste fluid and the culture time in Example 6.

The relationship between the concentration of triethanolamine or diethanolamine and the culture time is shown in FIG. 10.

The legends appeared in FIG. 10 are as follows:

"☐" ... Cornebacterium sp. N2 referring to triethanolamine

"+" ... Control referring to triethanolamine

"◇" ... Cornebacterium sp. N2 referring to diethanolamine

"△" ... Control referring to diethanolamine

As can be seen from FIG. 10, the concentration of triethanolamine or diethanolamine is decreased with the growth of the strain according to the present invention, triethanolamine and diethanolamine are completely decomposed after 9 days of the culture.

We claim:

1. A Cornebacterium sp. N which decomposes ethanolamine, said corynebacterium sp. N being at least one microorganism selected from the group consisting of Corynebacterium sp. N1, Cornebacterium sp. N2, Cornebacterium sp. N3, Cornebacterium sp. N4 and Cornebacterium sp. N5.

2. A process for treating an aqueous waste fluid containing ethanolamines by contacting the microorganisms according to claim 1 with the waste fluid containing ethanolamines.

3. The process of claim 2, wherein the aqueous waste fluid is an aqueous fluid of a machining oil.

4. The process of claim 2, wherein the aqueous waste fluid is subjected to a pretreatment and/or a post-treatment.

5. A process for treating an aqueous waste fluid, said process including the steps of (i) removing ingredients which inhibit the treatment of the waste fluid by a microorganism from the waste fluid, (ii) supplying the pretreated waste fluid to a semi-closed biological treatment tank equipped with an inlet and an outlet for a gas, (iii) adding at least one of the microorganisms of claim 1 to said tank to decompose ethanolamines in the waste fluid into an ammonium ion, (iv) adding an alkali to said tank to produce free ammonia at more than a pH of 10, (v) discharging the free ammonia as an ammonia gas through the outlet of said tank.

6. The process of claim 5, wherein the alkali is added to the biological treatment tank when ammonium ion concentration in the aqueous waste fluid becomes more than 800 ppm.

7. The process of claim 5, wherein the alkali is added to the biological treatment tank when the total concentration of ethanolamines in the form of triethanolamine and diethanolamine in the aqueous waste fluid becomes less than 50 ppm.

8. The process of claim 5, wherein the pH of the aqueous waste fluid treated by the microorganisms is adjusted to 10–13.

9. The process of claim 5, wherein the ingredients which inhibit the treatment of the waste fluid by the microorganisms are selected from the group consisting of preservatives and rust preventatives.

10. The process of claim 5, wherein the waste fluid in said tank is subjected to a post treatment selected from the group consisting of agglomerative precipitation and neutralization.

* * * * *